United States Patent [19]
Ellis et al.

[11] Patent Number: 6,093,185
[45] Date of Patent: Jul. 25, 2000

[54] EXPANDABLE PMR DEVICE AND METHOD

[75] Inventors: Louis Ellis, St. Anthony; Gary L. Hendrickson, Big Lake; Tara L. Brekke, Apple Valley, all of Minn.

[73] Assignee: SciMed Life Systems, Inc., Maple Grove, Minn.

[21] Appl. No.: 09/035,737

[22] Filed: Mar. 5, 1998

[51] Int. Cl.[7] .................................................. A61B 18/04
[52] U.S. Cl. .............................. 606/28; 606/32; 607/101; 607/122
[58] Field of Search .................................. 606/27–32, 41, 606/45–47, 49, 50; 607/96, 98–99, 101–102, 113, 119, 120, 122

[56] References Cited

U.S. PATENT DOCUMENTS

| 4,643,187 | 2/1987 | Okada . |
| 4,790,311 | 12/1988 | Ruiz . |
| 4,896,671 | 1/1990 | Cunningham et al. . |

(List continued on next page.)

FOREIGN PATENT DOCUMENTS

| 296 09 350 U 1 | 10/1996 | Germany . |
| 195 37 084 A 1 | 4/1997 | Germany . |
| WO 96/35469 | 11/1996 | WIPO . |
| WO 96/39963 | 12/1996 | WIPO . |
| WO 97/18768 | 5/1997 | WIPO . |
| WO 97/29803 | 8/1997 | WIPO . |
| WO 97/32551 | 9/1997 | WIPO . |
| WO 97/44071 | 11/1997 | WIPO . |

OTHER PUBLICATIONS

Mirhoseini et al., Abstract entitled "Transventricular Revascularization by Laser", *Lasers in Sugery and Medicine*, 2(2), 1982, 1 page.
Gal et al., Abstract entitled "Analysis of Photoproducts Free Radicals and Particulate Debris Generated . . . ", *Lasers in Surgery and Medicine*, 11(2) 1991, 1 page.
Isner, J., Abstract entitled "Right Ventricular Myocardial Infarction", *JAMA*, v259, n5, Feb. 5, 1988, 12 pages.
Pickering et al., Abstract entitled "Proliferative Activity in Peripheral and Coronary Atherosclerotic Plaque . . . ", *J. Clin. Invest.*, ISSN 0021–9738, Apr. 1993, 1 page.
Vineberg et al., "Creation of Intramyocardial Pathways to Channel Oxygenated Blood Between Ventricular Arteriolar Zones", *Canad. Med. Ass. J.*, vol. 96, Feb. 4, 1967, 3 pages.
Vineberg, A., "Results of 14 Years' Experience in the Surgical Treatment of Human Coronary Artery Insufficiency", *Canad. Med. Ass. J.*, vol. 92, Feb. 13, 1965, 8 pages.
Vineberg et al., "The Ivalon Sponge Procedure for Myocardial Revascularization", *Surgery*, vol. 47, No. 2, Feb. 1960, pp. 268–289.
Vineberg et al., "Treatment of Acute Myocardial Infarction by Endocardial Resection", *Surgery*, vol. 57, No. 6, Jun. 1965, pp. 832–835.
Walter et al., "Treatment of Acute Myocardial Infarction by Transmural Blood Suply from the Ventricular Cavity", *European Surgical Research*, 3:130–138 (1971).
Khazei et al., "Myocardial Canalization", *The Annnals of Thoracic Surgery*, vol. 6, No. 2, Aug. 1968, pp. 163–171.
Hershey et al., "Transmyocardial Puncture Revascularization", *Geriatrics*, Mar. 1969, pp. 101–108.
Press Release dated Oct. 21, 1996, "Doctor's Demonstrate Proof of Blood Flow Through Open TMR Channels Created with PLC Systems . . . ", 1 page.
Press/News Release dated Oct. 10, 1996, "Texas Fieart Institute Presents Study Comparing the Use of CO2 . . . ", 1 page.
Goldman et al., "Nonoperative Portacaval Shunt in Swine", *Investigative Radiology*, vol. 25, No. 5, May 1990, 5 pages.

*Primary Examiner*—Linda C. M. Dvorak
*Assistant Examiner*—Roy Gibson
*Attorney, Agent, or Firm*—Crompton, Seager & Tufte, LLC

[57] ABSTRACT

A PMR catheter including an elongate shaft having a proximal end and a distal end, and a conductor extending therethrough. An insulator disposed around the conductor. At least one conductive loop disposed at the distal end of the shaft. The conductive loop having an electrode disposed at its distal end.

8 Claims, 2 Drawing Sheets

U.S. PATENT DOCUMENTS

| | | | |
|---|---|---|---|
| 5,047,026 | 9/1991 | Rydell . | |
| 5,093,877 | 3/1992 | Aita et al. . | |
| 5,133,713 | 7/1992 | Huang et al. | 606/46 |
| 5,318,564 | 6/1994 | Eggers | 606/47 |
| 5,358,485 | 10/1994 | Vance et al. . | |
| 5,364,393 | 11/1994 | Auth et al. . | |
| 5,370,675 | 12/1994 | Edwards et al. . | |
| 5,380,316 | 1/1995 | Aita et al. . | |
| 5,389,096 | 2/1995 | Aita et al. . | |
| 5,403,311 | 4/1995 | Abele et al. . | |
| 5,423,806 | 6/1995 | Dale et al. | 606/15 |
| 5,437,665 | 8/1995 | Munro | 606/47 |
| 5,454,370 | 10/1995 | Avitall . | |
| 5,522,815 | 6/1996 | Durgin, Jr. et al. . | |
| 5,558,073 | 9/1996 | Pomeranz et al. . | |
| 5,591,159 | 1/1997 | Taheri . | |
| 5,593,405 | 1/1997 | Osypka . | |
| 5,593,406 | 1/1997 | Eggers et al. | 606/29 |
| 5,607,405 | 3/1997 | Decker et al. . | |
| 5,620,414 | 4/1997 | Campbell, Jr. . | |
| 5,645,082 | 7/1997 | Sung et al. | 128/897 |
| 5,672,174 | 9/1997 | Gough et al. . | |
| 5,681,308 | 10/1997 | Edwards et al. . | |
| 5,683,366 | 11/1997 | Eggers et al. . | |
| 5,697,882 | 12/1997 | Eggers et al. . | |
| 5,700,259 | 12/1997 | Negus et al. . | |
| 5,713,894 | 2/1998 | Murphy-Chutorian et al. . | |
| 5,725,521 | 3/1998 | Mueller . | |
| 5,725,523 | 3/1998 | Mueller . | |
| 5,730,127 | 3/1998 | Avitall . | |
| 5,807,392 | 9/1998 | Eggers | 606/31 |
| 5,836,947 | 11/1998 | Fleischman et al. | 606/47 |
| 5,843,152 | 12/1998 | Tu et al. | 607/122 |
| 5,902,272 | 5/1999 | Eggers et al. | 604/114 |

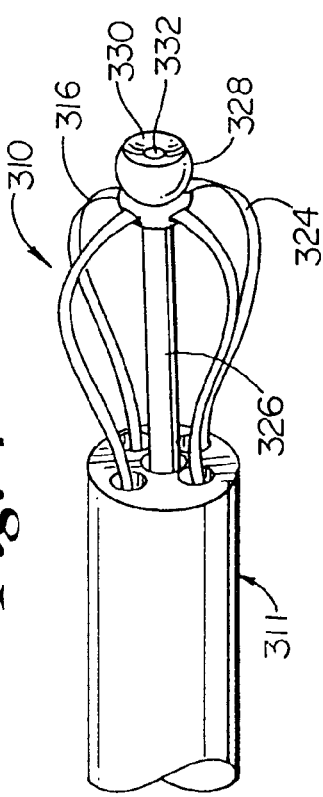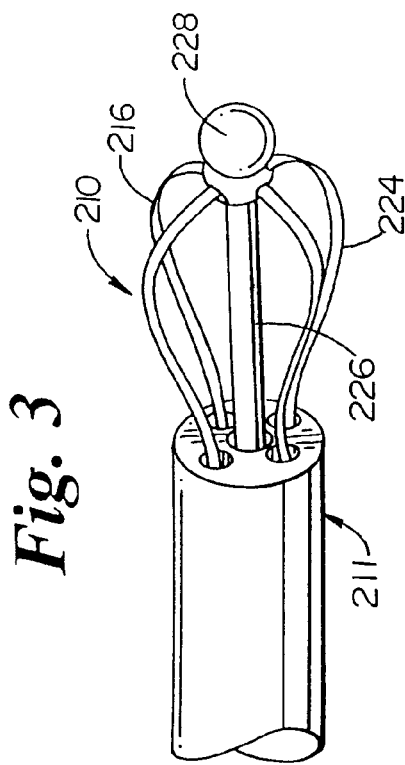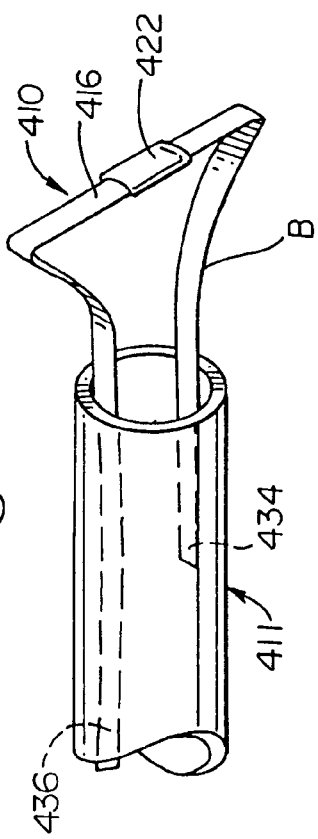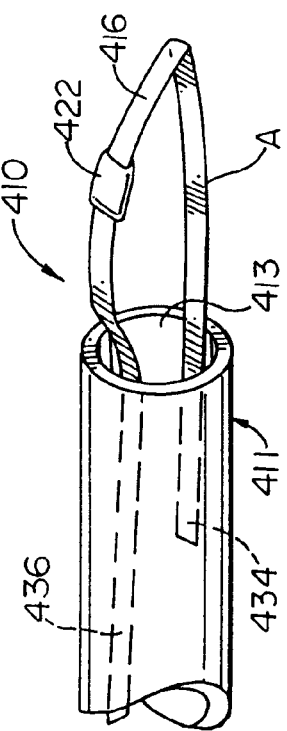

EXPANDABLE PMR DEVICE AND METHOD

RELATED APPLICATIONS

The present application is related to U.S. patent application Ser. No. 08/812,425, filed on Mar. 6, 1997, now U.S. Pat. No. 5,968,059 entitled TRANSMYOCARDIAL REVASCULARIZATION CATHETER AND METHOD, U.S. patent application Ser. No. 08/810,830, filed Mar. 6, 1997, now U.S. Pat. No. 5,938,632 entitled RADIOFREQUENCY TRANSMYOCARDIAL REVASCULARIZATION APPARATUS AND METHOD, herein incorporated by reference, and U.S. patent application Ser. No. 09/035,736, filed on Mar. 5, 1998, entitled PMR DEVICE AND METHOD.

FIELD OF THE INVENTION

The present invention relates generally to medical devices for forming holes in heart chamber interior walls in percutaneous myocardial revascularization (PMR) procedures. More specifically, the present invention relates to intravascular PMR devices having expandable distal loops deployable within heart chambers.

BACKGROUND OF THE INVENTION

A number of techniques are available for treating cardiovascular disease such as cardiovascular by-pass surgery, coronary angioplasty, laser angioplasty and atherectomy. These techniques are generally applied to by-pass or open lesions in coronary vessels to restore and increase blood flow to the heart muscle. In some patients, the number of lesions are so great, or the location so remote in the patient vasculature that restoring blood flow to the heart muscle is difficult. Percutaneous myocardial revascularization (PMR) has been developed as an alternative to these techniques which are directed at bypassing or removing lesions. Heart muscle may be classified as healthy, hibernating and "dead". Dead tissue is not dead but is scarred, not contracting, and no longer capable of contracting even if it were supplied adequately with blood. Hibernating tissue is not contracting muscle tissue but is capable of contracting, should it be adequately resupplied with blood. PMR is performed by boring channels directly into the myocardium of the heart.

PMR was inspired in part by observations that reptilian hearts muscle is supplied primarily by blood perfusing directly from within heart chambers to the heart muscle. This contrasts with the human heart, which is supplied by coronary vessels receiving blood from the aorta. Positive results have been demonstrated in some human patients receiving PMR treatments. These results are believed to be caused in part by blood flowing from within a heart chamber through patent channels formed by PMR to the myocardial tissue. Suitable PMR holes have been burned by laser, cut by mechanical means, and burned by radio frequency current devices. Increased blood flow to the myocardium is also believed to be caused in part by the healing response to wound formation. Specifically, the formation of new blood vessels is believed to occur in response to the newly created wound.

What would be desirable is a device capable of forming relatively wide holes in the wall of a heart chamber. Such a device would be capable of forming holes having a greater width than depth and thus limit the potential of perforation of the heart wall.

SUMMARY OF THE INVENTION

The present invention pertains to a device and method for performing percutaneous myocardial revascularization (PMR). The device includes an electrode which in most embodiments has a width greater than its depth such that it can be used to form craters in the myocardium of a patient's heart rather than channels. Craters are wounds in the myocardium of a patient's heart which have a width greater than their depth whereas channels can be considered to have a depth greater than their width. Holes in the myocardium are volumetric removals of material. The embodiments also include a loop to limit the penetration of the electrode.

In one embodiment, a catheter assembly is provided including an elongate shaft having a proximal and a distal end and a conductor extending through the shaft. An insulator is disposed around the conductor. A conductive loop is disposed at the distal end of the shaft. The conductive loop in turn has an electrode disposed at its distal end.

The catheter shaft can include a proximal portion and a more flexible distal portion. The proximal and distal portions can be stainless steel and Nitinol hypotubes respectively.

The loop is preferably formed from Nitinol which can be heat set to expand on introduction of the loop into a chamber of a patient's heart. The loop is preferably insulated with a material such as PTFE which can withstand high temperatures. The distal end of the loop, however, can act as an electrode if uninsulated.

The electrode can be positioned at the distal end of the loop. Preferably the electrode is substantially radiopaque such that it can readily be viewed by fluoroscopy.

In yet another embodiment, the loop is disposed proximate and proximally of the distal end of the shaft. An electrode is disposed at the distal end of the shaft. The shaft defines an elongate lumen. The lumen continues through the electrode such that contrast medium, growth factors or other drugs can be delivered to the wound created by the PMR procedure. The loop, if insulated, can act as a stop to limit the penetration of the electrode.

In yet another embodiment, the loop is retractable within the catheter shaft. In this embodiment, an elongate reciprocating shaft is disposed within a lumen defined by the catheter shaft. The reciprocating shaft is connected to at least one end of the loop, the reciprocating shaft is moveable between a first position and a second position such that in the second position, the loop has a greater transverse dimension than in the first position. In the first position, the reciprocating shaft is used to withdraw the loop into the catheter shaft lumen to reduce the transverse dimension of the loop for delivery and withdrawal from the heart.

In the method in accordance with the present invention, a catheter assembly is provided including an elongate shaft having a proximal end and a distal end. A transversely expandable conductive loop is disposed at the distal end of the shaft. An electrode is disposed on the loop. The loop is advanced to the myocardium of the patient's heart where the transverse dimension of the loop is allowed to expand as the loop enters a chamber of the patient's heart. The electrode is advanced to the endocardium and energized to form a crater in the myocardium. The electrode can be repeatedly advanced to the myocardium to form a plurality of craters. The electrode is preferably energized with radiofrequency energy to create an arc which ablates or removes tissue.

BRIEF DESCRIPTION OF THE DRAWINGS

FIG. 3 is a perspective view of yet another alternate embodiment of the distal end of the PMR catheter;

FIG. 4 is a perspective view of yet another alternate embodiment of the distal end of the PMR catheter;

FIG. 5 is a perspective view of yet another alternate embodiment of the distal end of the PMR catheter; and FIG. 6 is a view of the distal end of the PMR catheter of FIG. 5 shown in a deployed position.

DETAILED DESCRIPTION OF THE INVENTION

Figure 1:
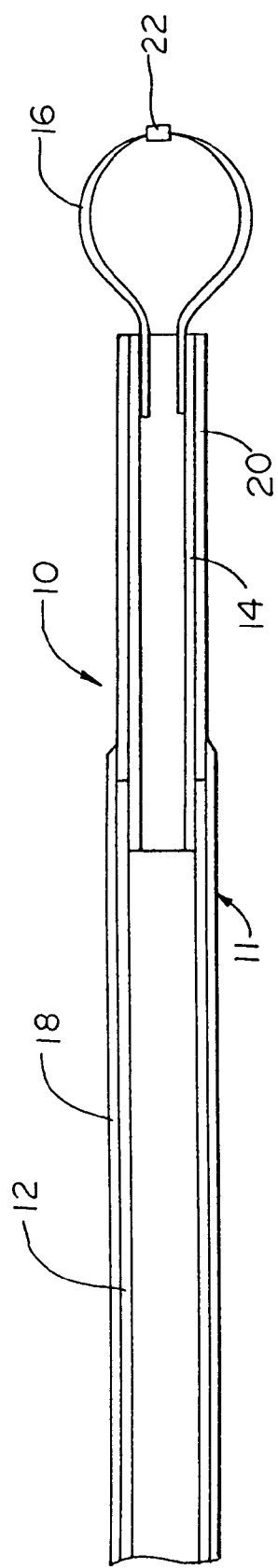
FIG. 1 is a longitudinal, cross-sectional view of a PMR catheter in accordance with the present invention.

Referring now to the drawings wherein like reference numerals represent like elements throughout the several views, FIG. 1 is a longitudinal, cross-sectional view of a catheter 10 in accordance with the present invention. Catheter 10 includes an elongate shaft 11 having a proximal portion 12 and a distal portion 14. A loop 16 is connected to catheter 10 at the distal end of shaft 11. Proximal portion 12 of shaft 11 is preferably formed from a metallic member such as a stainless steel hypotube. Portion 14 is preferably formed from a metallic member such as a Nitinol hypotube. Loop 16 is preferably formed from, for example, a Nitinol ribbon having a cross section of about 0.003 inches by about 0.005 inches as well. The connections between proximal shaft 12, distal shaft 14 and loop 16 should be formed from a solder or other conductive material such that a conductive path can be formed through shaft 11 to loop 16 for conductance of RF energy.

As one skilled in the art would recognize, an RF generator can be connected to the proximal end of shaft 11 to deliver radio frequency energy to loop 16. The strength of the RF field delivered to loop 16 should be sufficient to create the desired wound in a patient's myocardium when performing percutaneous myocardial revascularization (PMR).

To guard against injury to the vasculature through which catheter 10 is advanced, shaft 11 is insulated. Proximal portion 12 can be insulated by a layer of polyethylene 18. Distal portion 14 can be insulated by a layer of polyimide 20. These insulative materials are illustrative examples only, as other biocompatible materials may advantageously be used as insulators.

Loop 16 is preferably heat set to expand from a compressed position to be passed through a guide catheter to, for example, the left ventricle of the patient's heart. Loop 16 is preferably heat set such that as loop 16 enters the left ventricle, it will expand to a size greater than the diameter of the guide catheter lumen through which loop 16 was advanced.

A radiopaque marker 22 is preferably disposed at the distal end of loop 16. Marker 22 is preferably formed from a radiopaque material such as gold or platinum. Marker 22 should be conductively connected to loop 16 to enable marker 22 to act an electrode to deliver RF energy to a patient's myocardium. If it is desired to form craters in the patient's myocardium, the distance which marker 22 extends distally from loop 16 should be less than the maximum transverse dimension of marker 22 (a crater is a hole having a width greater than its depth).

To focus the RF energy on marker 22, loop 16 can be insulated with a material such as heat shrink PTFE. If a portion of loop 16, for example, adjacent its distal end, is left uninsulated, the uninsulated portion of loop 16 can act as an electrode. In such an instance, a very wide crater can be formed. The width of the crater being approximately equal to the transverse dimension of the uninsulated portion of loop 16. Since loop 16 can have a transverse dimension greater than that of the guide catheter lumen through which it is advanced, the crater can have a width which is in turn, greater than the diameter of the guide catheter lumen. It can be appreciated that to the extent that the transverse portion of loop 16 is insulated, it can act as a stop limiting the penetration of marker 22.

It should be noted that marker 22 and loop 16 can be pressured against the endocardium during the PMR procedure. During the PMR procedure, since the heart continues to beat, marker 22 will be motion when in contact with the heart. To absorb the movement of the heart and keep marker 22 in contact with the heart wall, it can be appreciated that loop 16 can act as a shock absorber to dampen the change in force incident to marker 22 as the heart beats.

Figure 2:
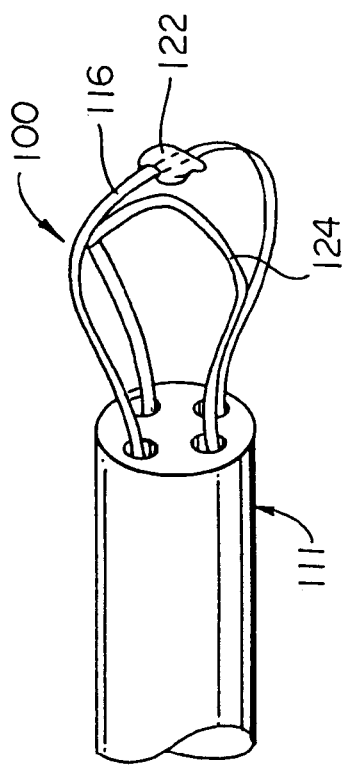
FIG. 2 is a perspective view of an alternate embodiment of the distal end of the PMR catheter.

FIG. 2 is a perspective view of a distal end of an alternate embodiment 100 of a catheter in accordance with the present invention. Catheter 100 includes a shaft 111 and a loop 116 extending distally therefrom having a radiopaque marker 122 disposed on the distal end thereof. A second loop 124 extends from the distal end of shaft 111 to proximate, and proximal of the distal end of loop 116. It can be appreciated that if a portion of second loop 124 were not insulated and it were connected to ground or a lower voltage than loop 116, that it could act as a second pole to create a bi-polar RF ablation device (a second pole could be added to each of the other embodiments disclosed herein as well). A distal portion of loop 116, as well as marker 122, can be used as an electrode if left uninsulated. Insulating loop 124, loop 124 can act as a stop limiting penetration of loop 116 into the myocardium during the PMR procedure. The various components of catheter 100 can be formed from the same materials as catheter 10 and assembled in a similar manner.

FIG. 3 shows a perspective view of a distal end of yet another embodiment 210 of the catheter in accordance with the present invention. Catheter 210 includes a shaft 211 and a distal shaft extension 226. Disposed at the distal end of extension 226 is a tip 228. Shaft 226 is preferably formed from a metal such as Nitinol. Tip 228 can be a ball shaped tip formed from, for example, stainless steel. Shaft extension 226 and ball tip 228 are connected to shaft 211 by soldering or other means to form a conductive path from shaft 211 through extension 226 into ball tip 228. Ball tip 228 can then act as an electrode to form holes in the myocardium of the patient's heart during the PMR procedure.

Catheter 210 includes a first loop 216 and a second loop 224. Preferably loops 216 and 224 as well as extension 226 are insulated by a material such as heat shrink PTFE. When loops 216 and 224 are insulated, they can act as stops limiting the penetration of tip 228 into the myocardium of the patient's heart.

FIG. 4 shows a perspective view of the distal end of yet another embodiment 310 of the catheter in accordance with the present invention. Catheter 310 is substantially similar to catheter 210, having a shaft 311, a conductive shaft extension 326 and electrode tip 328. Catheter 310 also includes first and second loops 316 and 324, respectively.

Each of the elements 310 are formed from the same materials in essentially the same way as that of the previous embodiments and, in particular, of catheter 210. Tip 326, however, includes a truncated surface 330. In addition, a lumen extends through the entire length of the catheter exiting at opening 332 in tip 328. During PMR, contrast media, growth factor or other drugs can be delivered to the myocardium of the patient's heart through the lumen.

FIG. 5 shows a distal end of yet another embodiment 410 of the catheter in accordance with the present invention.

Catheter 410 includes a shaft 411 which defines a lumen 413 extending between the proximal and distal ends of shaft 411. Loop 416 extends distally from lumen 413. Loop 416 has a first end 434 and a second end 436 which extends to the proximal end of shaft 411. End 434 is anchored to shaft 411 proximate the distal end of shaft 411. A marker 422 can be disposed on loop 416. Loop 416 is preferably formed from a metallic ribbon such as a Nitinol ribbon having cross-sectional dimensions of about 0.003 inches by about 0.005 inches. At least one end of loop 416 is connected to a radio frequency generator. Loop 416 can also be stainless steel, cold worked and heat treated into the desired geometry.

As shown in FIG. 5, loop 416 is disposed in an advancement position A. In FIG. 6, loop 416 is shown in a deployed position B. Loop 416 can be shifted from position A to position B by advancing end 436 distally. Loop 416 can be shifted from position B to position A by pulling end 436 proximally.

As can be seen in FIG. 6, loop 416 has a substantial transversely extending distal portion. This configuration can be obtained by heat setting or pre-forming loop 416 as known to those skilled in the art. It can be appreciated that if the substantially transversely extending portion of loop 416 is left uninsulated to form an electrode, an electrode can be delivered during the PMR procedure which is substantially wider than the diameter of the guide catheter lumen through which it is advanced. Loop 416 can, however, be insulated such that only marker 422 acts as an electrode.

In use, each of the catheters of the present invention is preferably advanced percutaneously through a guide catheter extending through the aorta into the left ventricle of a patient's heart. It can be appreciated that the various embodiments can be advanced into other heart chambers as well. Once the electrode has been advanced to the patient's heart, RF energy is delivered to the electrode. The electrode is then repeatedly advanced into the patient's myocardium to create holes therein.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method of performing PMR, comprising the steps of:
    providing a catheter assembly including an elongate shaft having a proximal end and a distal end, and a transversely expandable conductive loop at the distal end, the loop having an electrode disposed thereon;
    advancing the loop to the myocardium of a patient's heart;
    increasing the transverse dimension of the loop;
    energizing the electrode to wound the myocardium; and
    advancing the electrode into the myocardium.

2. The method in accordance with claim 1, further comprising the step of repeatably advancing the electrode into the myocardium.

3. The method in accordance with claim 1, wherein the electrode is energized with RF energy.

4. A catheter assembly comprising:
    an elongate shaft having a proximal end and a distal end and including a conductor therein, wherein the shaft includes a proximally disposed stainless steel hypotube and a distally disposed Nitinol hypotube;
    an insulator disposed around the conductor;
    a conductive loop attached to the conductor, disposed at the distal end of the shaft, the conductive loop having a distal end; and
    an electrode disposed at the distal end of the loop.

5. A catheter assembly comprising:
    an elongate shaft having a proximal end and a distal end and including a conductor therein;
    an insulator disposed around the conductor;
    a loop attached to the conductor, disposed proximate and proximally of the distal end of the shaft; and
    an electrode disposed at the distal end of the shaft, wherein the electrode includes a ball tip.

6. A catheter assembly comprising:
    an elongate shaft having a proximal end and a distal end and including a conductor therein, wherein the shaft comprises a lumen extending therethrough;
    an insulator disposed around the conductor;
    a conductive loop attached to the conductor, disposed at the distal end of the shaft, the conductive loop having a distal end; and
    an electrode disposed at the distal end of the shaft, wherein the electrode includes a truncated tip in fluid communication with the lumen of the elongate shaft.

7. The catheter assembly of claim 6, wherein contrast media is dispensed through the lumen and the electrode.

8. The catheter assembly of claim 6, wherein growth factor drugs are dispensed through the lumen and the electrode.

* * * * *